US00PP08215P

United States Patent [19]

Moretti

[11] Patent Number: Plant 8,215

[45] Date of Patent: Apr. 27, 1993

[54] GOLDEN PYGMY BARBERRY PLANT NAMED BOGOZAM

[75] Inventor: Nicholas R. Moretti, Geneva, Ohio

[73] Assignee: James W. Zampini, Perry, Ohio

[21] Appl. No.: 765,677

[22] Filed: Sep. 26, 1991

[51] Int. Cl.[5] ..... A01H 5/00

[52] U.S. Cl. ..... Plt./58

[58] Field of Search ..... Plt./58

*Primary Examiner*—James R. Feyrer
*Assistant Examiner*—Erich Veitenheimer
*Attorney, Agent, or Firm*—Burns, Doane, Swecker & Mathis

[57] ABSTRACT

A new and distinct variety of golden pygmy barberry plant named Bogozam is provided. The new variety can be readily distinguished from its parents, *Berberis thunbergii* 'Atropurpurea Nana' and *Berberis thunbergii* 'Aurea' (both nonpatented in the United States). For instance, the new variety forms a dwarf, compact, broad low-mounding plant; generally forms mature leaves of a brighter and more intense golden coloration; generally forms new growth having a brighter and more intense red coloration; generally exhibits a rapid growth rate between internodes of a relatively short length and a dense growth habit; and is more tolerant to sun scald. The new variety is particularly well suited for growing as attractive ornamentation in the landscape.

5 Drawing Sheets

SUMMARY OF THE INVENTION

The new and distinct variety of Berberis plant was discovered during 1971 from among seedlings being grown in a cultivated area tended by man. Such seedling of the new variety was the product of controlled crosses between *Berberis thunbergii* 'Atropurpurea Nana' and *Berberis thunbergii* 'Aurea' which had been made by me and were being grown at the Moretti Nursery located at 3525 Blackmore Road, Perry, Ohio 44081 in Zone 6a.

My attention was initially attracted to the new variety since it was found to exhibit a combination of characteristics which differ significantly form those of its parents and all other cultivars derived from *Berberis thunbergii* of which I am aware. Had I not discovered and preserved this new plant it would have been lost to mankind.

It has been found that the new and distinct golden pygmy barberry plant of the present invention exhibits the following combination of characteristics:

(a) exhibits a dwarf, generally compact, broad, and low-mounding growth habit,
(b) forms mature leaves of a brighter and more intense golden coloration than its parent *Berberis thunbergii* 'Aurea',
(c) forms new growth having a brighter and more intense red coloration than its parent *Berberis thunbergii* 'Aurea',
(d) exhibits a rapid growth rate between internodes of a relatively short length, and
(e) generally is more tolerant to sun scald than its parent *Berberis thunbergii* 'Aurea'.

Plants of the new variety have been asexually reproduced at Perry, Ohio, through the use of softwood cuttings. Propagation by this method has proven to be 99 percent successful. The characteristics of the new variety have been found to be strictly transmissible by such asexual propagation from one generation to another.

The new variety has been named the Bogozam variety. Also, plants of the new variety will be marketed by Lake County Nursery, Inc. of Perry, Ohio, under the Bonanza Gold trademark.

BRIEF DESCRIPTION OF THE PHOTOGRAPHS

The accompanying photographs show as nearly true as it is reasonably possible to make the same in color illustrations of this character, typical specimens of the plant and plant parts of the new variety during various stages of development. The specimens depicted were grown at Perry, Ohio.

DETAILED DESCRIPTION

Figure 1:
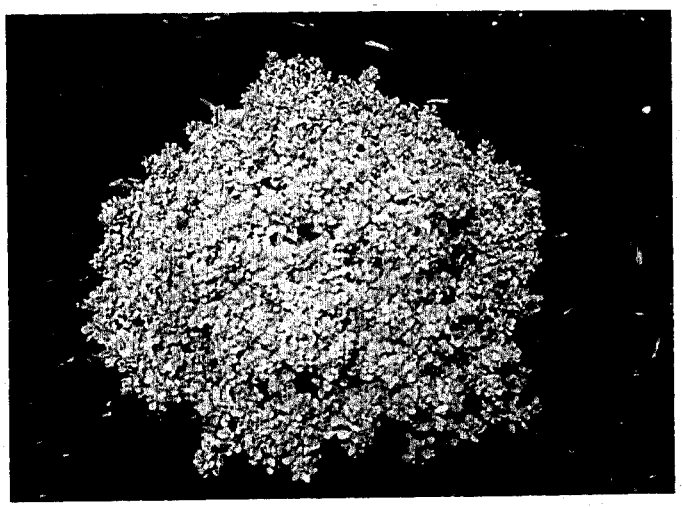
FIG. 1 illustrates an eight year-old plant of the new variety during the summer growing season wherein the golden coloration of mature foliage is apparent.
Figure 2:
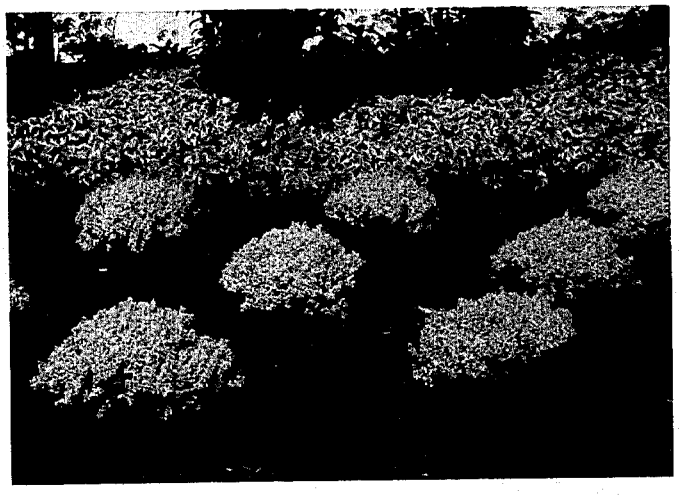
FIG. 2 illustrates at the foreground a group planting of eight year-old plants of the new variety during the summer growing season.
Figure 3:
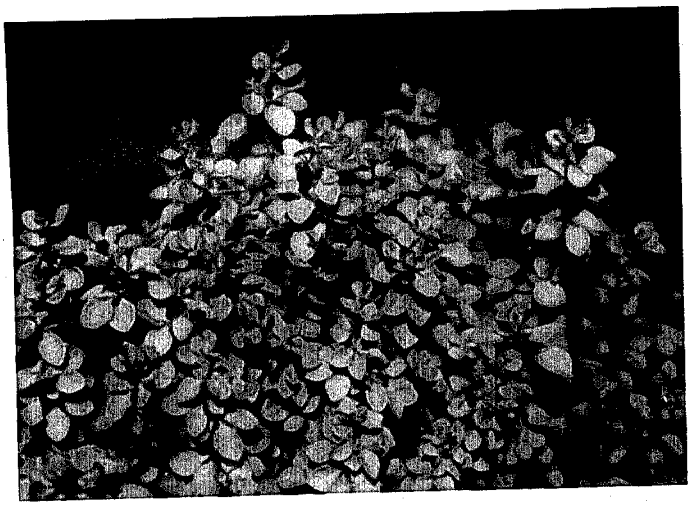
FIG. 3 illustrates a close-up view (taken from the side) of the new variety during the summer growing season showing the tight scaffold branching structure and the red coloration of leaves and shoots of the new season's growth.
Figure 4:
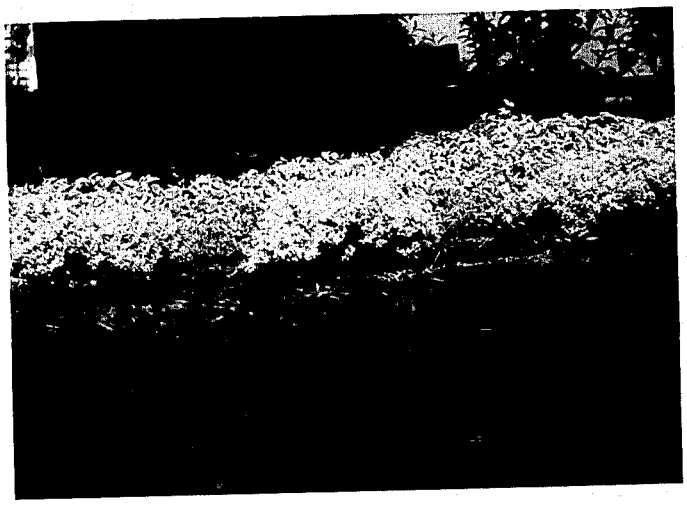
FIG. 4 illustrates in the foreground of the mulched area a view (taken from the side) of the new variety during the summer growing season showing its broad, compact, and low-mounding growth habit.
Figure 5:
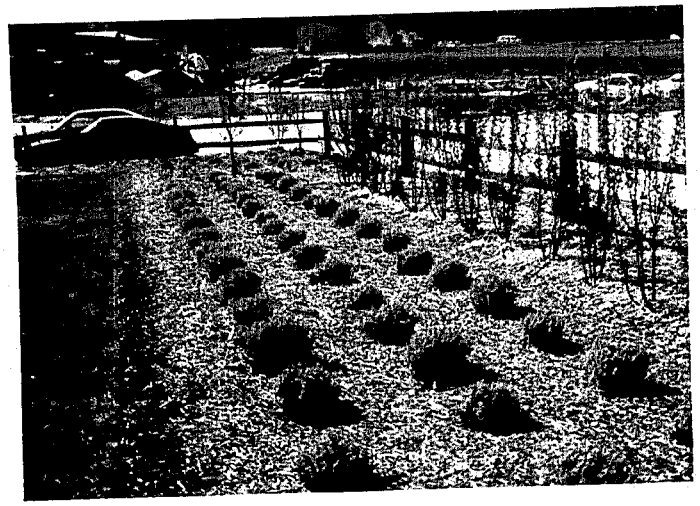
FIG. 5 illustrates a mass planting of eight year-old plants of the new variety during the early spring season showing that the initial spring growth on mature stems emerges in a green coloration.
Figure 6:
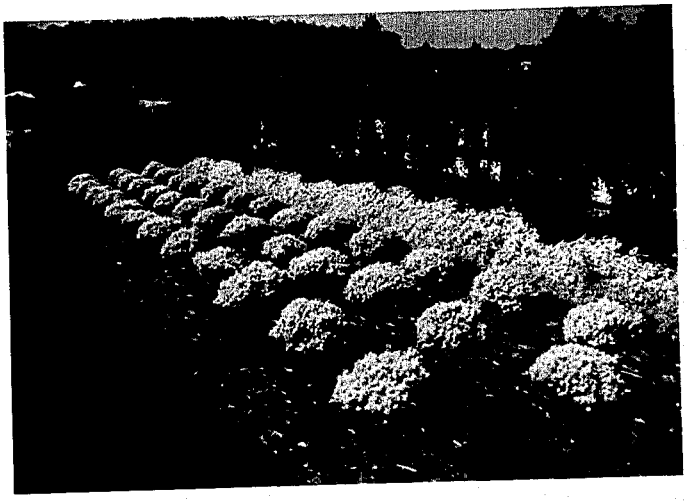
FIG. 6 illustrates the same mass planting of eight year-old plants of the new variety during the summer growing season wherein the golden coloration of mature foliage is apparent.
Figure 7:
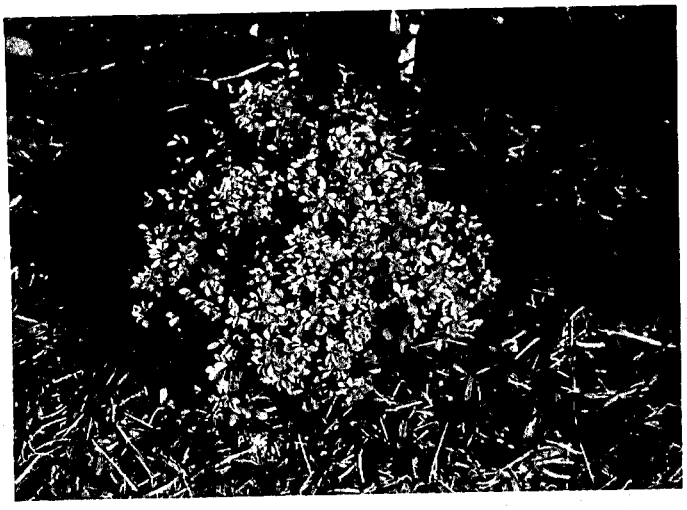
FIG. 7 illustrates a plant of the new variety during the fall season. The photograph was taken during October and the coloration is attributable to the fall environment.
Figure 8:
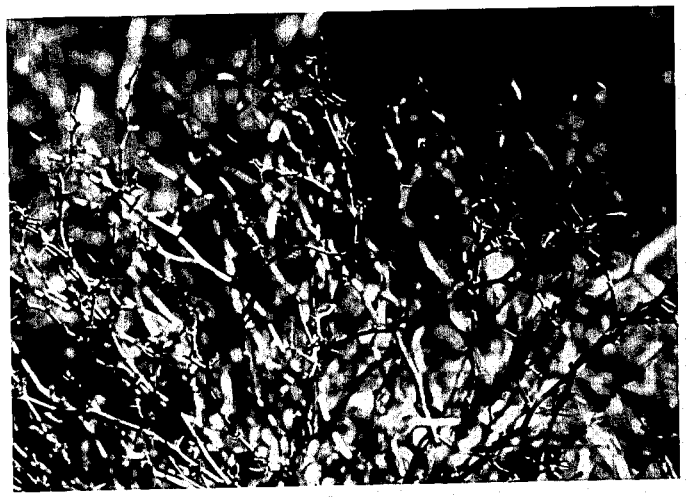
FIG. 8 illustrates a close-up view (taken from the side) of the new variety taken during the winter showing the tight scaffold branching structure.
Figure 9:
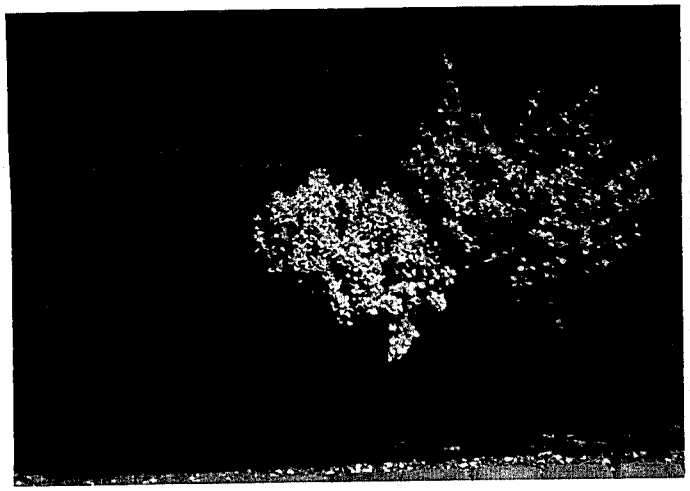
FIG. 9 illustrates for comparative purposes during the summer a four year-old container grown plant of the new variety (center) and its parents, *Berberis thunbergii* 'Atropurpurea Nana' on the left and *Berberis thunbergii* 'Aurea' on the right. The disparity in plant size, growth habit, and leaf coloration is apparent.
Figure 10:
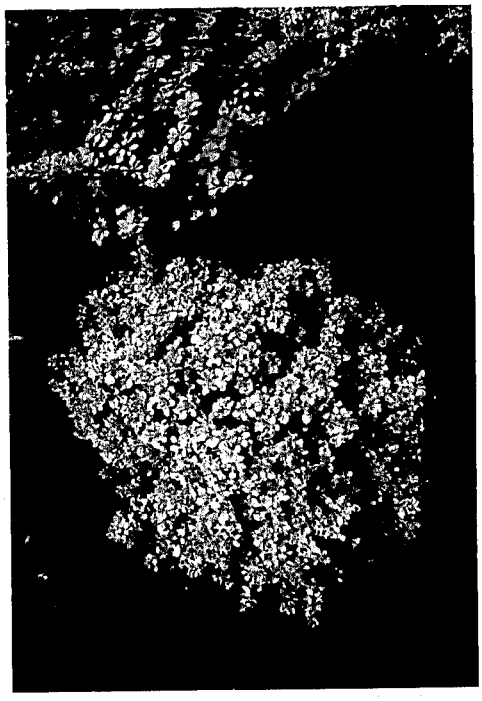
FIG. 10 illustrates for comparative purposes during the summer a close-up view of the foliage of four year-old container grown plants of the new variety at the bottom and top right; the *Berberis thunbergii* 'Aurea' parent at the left; and the *Berberis thunbergii* 'Atropurpurea Nana' parent at the middle right. The disparity in growth habit and leaf coloration is apparent.

The chart used in the identification of colors is that of The Royal Horticultural Society (R.H.S. Colour Chart). Other references to color are to be accorded their ordinary dictionary significance. The descriptions are based upon plants grown at Perry, Ohio.

The original plant of the new variety exhibits a highly manageable dwarf growth habit and presently is approximately 12 inches tall and approximately 28 inches wide. The new variety exhibits a rapid growth rate while well retaining a compact, broad, and low-mounding growth habit. In comparison, its parent, *Berberis thunbergii* 'Aurea' is slow growing with an upright growth habit, and its parent *Berberis thunbergii* 'Atropurpurea Nana' is a slow grower with a low and spreading growth habit. The new variety is expected to reach a height of approximately 18 inches and a width of approximately 36 inches at full maturity.

The vegetative and reproductive parts of the new variety are in most respects typical of the genus. The entire, alternate, simple, leaves are broadly obovate to broadly spatulate. The spine-tipped leaves are borne in clusters along the branches and are approximately ½ to ¾ inch in length narrowing at the base to a petiole which is approximately 1/16 to ¼ inch in length. The immature leaves of the new variety during mid-season commonly range in coloration from approximately that of Yellow Group 6A to 6C, 7A to 7C, and 10A on the upper surface, and tend to be somewhat paler on the under surface with a coloration which approximates that of Yellow Group 10B to 10D. Leaves on mature stems commonly exhibit a coloration which approximates that of Green Group 143A on the upper surface and tend to be of a somewhat paler coloration on the under surface which approximates that of Green Group 139D. Emerging new growth has a distinctly red coloration that is of a brighter and more intense shade than that of its parent *Berberis thunbergii* 'Aurea'. The coloration of the outer leaf margin of the leaves and the leaf shoots commonly approximates that of Red Group 43A. Such coloration generally is more intense at the stem internodes. During the fall season the foliage commonly assumes a coloration which approximates that of the Red Group 48B, 49B, and 49C. Foliage colors are specified for plants of the new variety when grown in full sun. If grown in the shade, the foliage coloration will not be as intense in accordance with a trait shared by plants of the genus.

A common trait of its parent *Berberis thunbergii* 'Aurea' is its susceptibility to summer sun scald, which is an injury of woody plants characterized by a localized death of plant tissue attributable to the combined action of heat and light. When affected by sun scald, *Berberis thunbergii* 'Aurea' generally forms deformed leaves and/or drops its foliage leaving a plant which exhibits an unattractive spindly appearance. While the new variety also can be affected by sun scald, it is more tolerant to heat and light and therefore is not affected as severely as its parent and does not exhibit the same degree of unfavorable side effects commonly associated with sun scald. Immature twigs vary in coloration from red at the tip to brown at the base and generally exhibit a coloration which approximates that of the Brown Group 200B. The coloration of the leaf buds tends to match the stem coloration. Older stems tend to be light brown in coloration and generally approximate the coloration of Grey-Brown Group 199D with cordovan brown striations.

During the blooming season the new variety of the present invention bears pale yellow inconspicuous flowers and in the fall it bears red ellipsoidal berries, both of which are typical of the genus.

I claim:

1. A new and distinct variety of golden pygmy barberry plant which exhibits the following combination of characteristics:

(a) exhibits a dwarf, generally compact, broad, and low-mounding growth habit,
(b) forms mature leaves of a brighter and more intense goldlen coloration than its parent *Berberis thunbergii* 'Aurea',
(c) forms new growth having a brighter and more intense red coloration than its parent *Berberis thunbergii* 'Aurea',
(d) exhibits a rapid growth rate between internodes of a relatively short length, and
(e) generally is more tolerant to sun scald than its parent *Berberis thunbergii* 'Aurea';

substantially as herein shown and described.

* * * * *